US006599484B1

(12) United States Patent
Zigler et al.

(10) Patent No.: US 6,599,484 B1
(45) Date of Patent: Jul. 29, 2003

(54) APPARATUS FOR PROCESSING RADIONUCLIDES

(75) Inventors: Steven S. Zigler, Knoxville, TN (US); Thomas Mangner, Chelsea, MI (US); Joseph C. Matteo, Knoxville, TN (US)

(73) Assignee: CTI, Inc., Knoxville, TN (US)

( * ) Notice: Subject to any disclaimer, the term of this patent is extended or adjusted under 35 U.S.C. 154(b) by 0 days.

(21) Appl. No.: 09/569,780

(22) Filed: May 12, 2000

(51) Int. Cl.[7] ............................................... B01J 19/00
(52) U.S. Cl. ..................... 422/130; 422/99; 422/102; 422/129; 422/138
(58) Field of Search ....................... 422/99, 102, 104, 422/129, 130, 108, 109, 138; 436/57, 59, 804, 55

(56) References Cited

U.S. PATENT DOCUMENTS

| 3,754,999 | A |   | 8/1973  | Merges            |         |
|-----------|---|---|---------|-------------------|---------|
| 4,239,970 | A |   | 12/1980 | Eckhardt et al.   |         |
| 4,605,536 | A | * | 8/1986  | Kuhnert et al.    | 422/99  |
| 5,109,160 | A |   | 4/1992  | Evers             |         |
| 5,254,328 | A |   | 10/1993 | Herscheid et al.  |         |
| 5,302,347 | A | * | 4/1994  | Van Den Berg et al. | 422/67 |
| 5,415,843 | A | * | 5/1995  | Andersson         | 422/102 |
| 5,455,175 | A | * | 10/1995 | Wittwer et al.    | 435/286.1 |
| 5,466,603 | A | * | 11/1995 | Meehan et al.     | 435/285.1 |
| 5,770,030 | A |   | 6/1998  | Hamacher et al.   | 205/43  |
| 5,795,547 | A | * | 8/1998  | Moser et al.      | 422/104 |
| 5,942,432 | A | * | 8/1999  | Smith et al.      | 435/303.1 |
| 6,130,926 | A |   | 10/2000 | Amini             |         |
| 6,271,024 | B1 | * | 8/2001 | Sve et al.        | 435/303.1 |
| 6,296,814 | B1 | * | 10/2001 | Bonk et al.       | 422/196 |
| 6,337,435 | B1 | * | 1/2002 | Chu et al.        | 136/242 |

OTHER PUBLICATIONS

Link, Jeanne et al., "Introduction: State of the Art in Automated Synthesis of Short–Lived Radiopharmaceuticals," Targetry '91, pp. 174–185.

* cited by examiner

Primary Examiner—Jill Warden
Assistant Examiner—Dwayne K Handy
(74) Attorney, Agent, or Firm—Pitts & Brittian, P.C.

(57) ABSTRACT

An apparatus for processing radionuclides which generally includes a reaction vessel and a block. The reaction vessel includes a test tube and a cover secured to a top portion of the test tube. The cover defines at least one opening for receiving an input tube therethrough such that raw materials, reagents, gases and products can be introduced into or removed from the test tube. The block defines a vessel receptacle, an upper temperature changing means and a lower temperature changing means. The vessel receptacle defines an upper zone and a lower zone and is configured to receive the reaction vessel therein in a manner such that an upper zone space is defined between an exterior of the reaction vessel and an inner wall of the vessel receptacle in the upper zone. Likewise, a lower zone space is defined between an exterior of the reaction vessel and inner wall of the vessel receptacle in the lower zone. The upper temperature changing means serves to alter the temperature of gas in the upper zone space and the lower temperature changing means serve to alter the temperature of gas in said lower zone space.

23 Claims, 5 Drawing Sheets

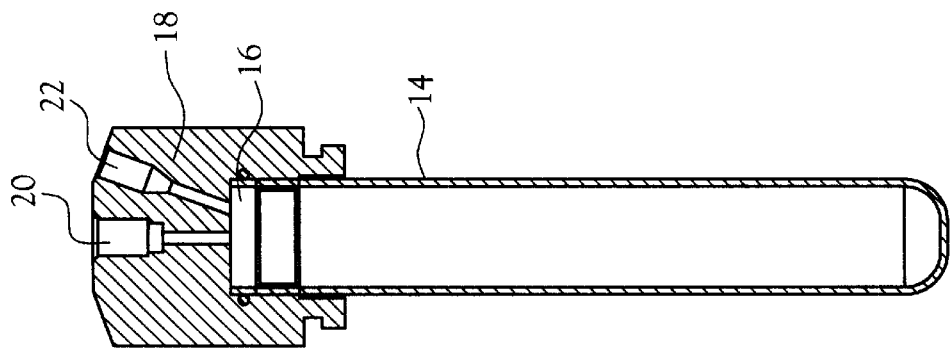
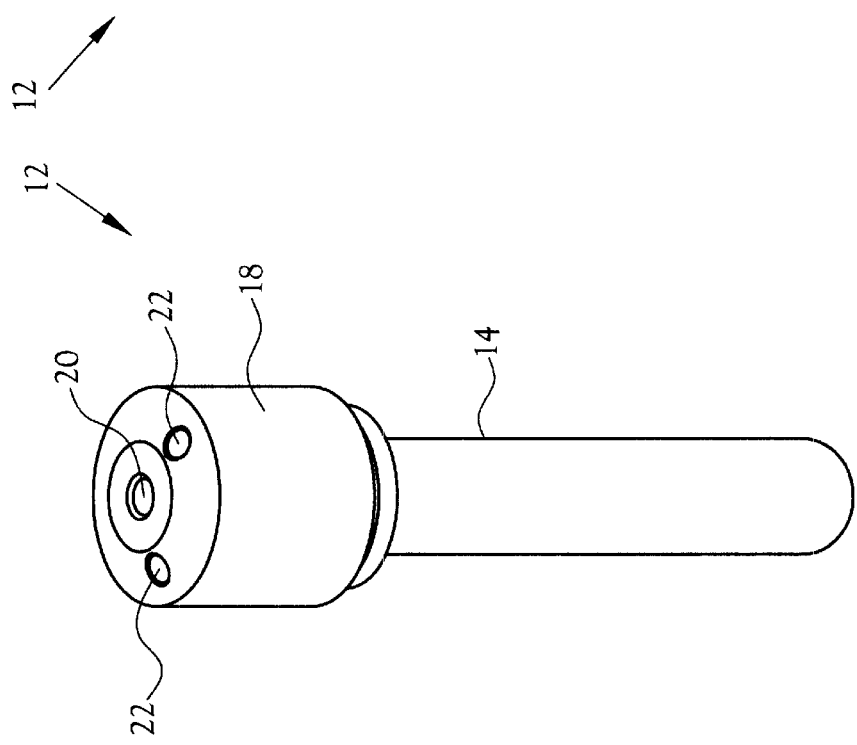

APPARATUS FOR PROCESSING RADIONUCLIDES

TECHNICAL FIELD

This invention relates to the field of apparatuses for processing radionuclides.

BACKGROUND ART

Positron Emission Tomography (PET) is a powerful tool for diagnosing and treatment planning of many diseases wherein radiopharmaceuticals or radionuclides are injected into a patient to diagnose and assess the disease. Accelerators are used to produce the radioisotopes used in PET. Generally, an accelerator produces radioisotopes by accelerating a particle beam and bombarding a target material, housed in a target system, with the particle beam.

In certain cases, the product of bombardment needs to be further processed to produce a substance suitable for injection into the human body. For example, [$^{18}$F]fluoride ions are commonly produced with an accelerator and appropriate target. These ions must be farther processed to produce [$^{18}$F]FDG (x2-deoxy-2-fluoro-D-glucose), this process is typically referred to as radiosynthesis. Because of the radioactivity of [$^{18}$F], it is desirable to automate as much of the processing as possible to avoid human exposure to radiation.

One apparatus which is currently employed includes a glassy carbon reaction vessel in a heating block fabricated from aluminum. The reaction vessel is in direct contact with the heating block to heat and cool the vessel. This system, as well as many other aspects of automated synthesis, is discussed in a paper entitled "Introduction: State of Art in Automated Syntheses of Short-Lived Radiopharmaceuticals" by Jeanne M. Link, John C. Clark and Thomas J. Ruth, *Targetry* '91. pp 174–185. More specifically, at page 180, Nebeling discusses this system indicating a heating/cooling range of −200° C. to +200° C. and a time span of approximately 1½ minutes to change the temperature. Further, at page 183, Nebeling refers to an automated FDG system which is self cleaning. He specifically indicated that the key to success was the use of the glassy carbon reaction vessel.

Although the prior art system has proven somewhat successful for the production of FDG, the design of this system does not allow for rapid temperature changes or control of temperature gradients. Further, thermocouples do not directly measure the temperature of the solution, rather they measure the temperature of the heater block. Moreover, the glassy carbon reaction vessel is custom machined and expensive.

German Patent DE 195 15 212 A1 discloses a method for processing [$^{18}$F] fluoride ions to produce [$^{18}$F]FDG, which can be employed with an automated synthesis device.

Therefore, it is an object of the present invention to provide an apparatus for processing radionuclides which provides the capability of rapid temperature change.

Further, it is an object of the present invention to provide an apparatus for processing radionuclides which provides the capability to heat and/or cool two different regions of the reaction vessel.

It is another object of the present invention to provide an apparatus for processing radionuclides which utilizes infrared temperature sensing.

It is yet another object of the present invention to provide an apparatus for processing radionuclides wherein the reaction vessel is closed.

Moreover, it is an object of the present invention to provide an apparatus for processing radionuclides wherein the reaction vessel is disposable.

DISCLOSURE OF THE INVENTION

Other objects and advantages will be accomplished by the present invention which serves to process radionuclides in an apparatus which utilizes a reaction vessel for processing the radionuclides therein. The apparatus for processing radionuclides is generally comprised of a block which defines a vessel receptacle, an upper temperature changing means and a lower temperature changing means. The vessel receptacle defines an upper zone and a lower zone and is configured to receive the reaction vessel therein in a manner such that an upper zone space is defined between an exterior of the reaction vessel and an inner wall of the vessel receptacle in the upper zone. Likewise, a lower zone space is defined between an exterior of the reaction vessel and inner wall of the vessel receptacle in the lower zone. The upper temperature changing means serves to alter the temperature of gas in the upper zone space and the lower temperature changing means serve to alter the temperature of gas in said lower zone space. The temperature in the upper and lower zone are independently controllable.

BRIEF DESCRIPTION OF THE DRAWINGS

The above mentioned features of the invention will become more clearly understood from the following detailed description of the invention read together with the drawings in which:

FIG. 2 is a perspective view of the reaction vessel;

FIG. 3 is a side elevation view, in section, of the reaction vessel, taken at 3—3 of FIG. 2;

BEST MODE FOR CARRYING OUT THE INVENTION

An apparatus for processing radionuclides incorporating various features of the present invention is illustrated generally at 10 in the figures. The apparatus for processing radionuclides 10 is designed to provide the capability of rapid temperature change and to heat and/or cool two different regions of the reaction vessel. Moreover, in the preferred embodiment, the apparatus for processing radionuclides 10 is designed to utilize infrared temperature sensing and/or thermocouple sensing thereby providing real-time temperature measurements.

Figure 1:
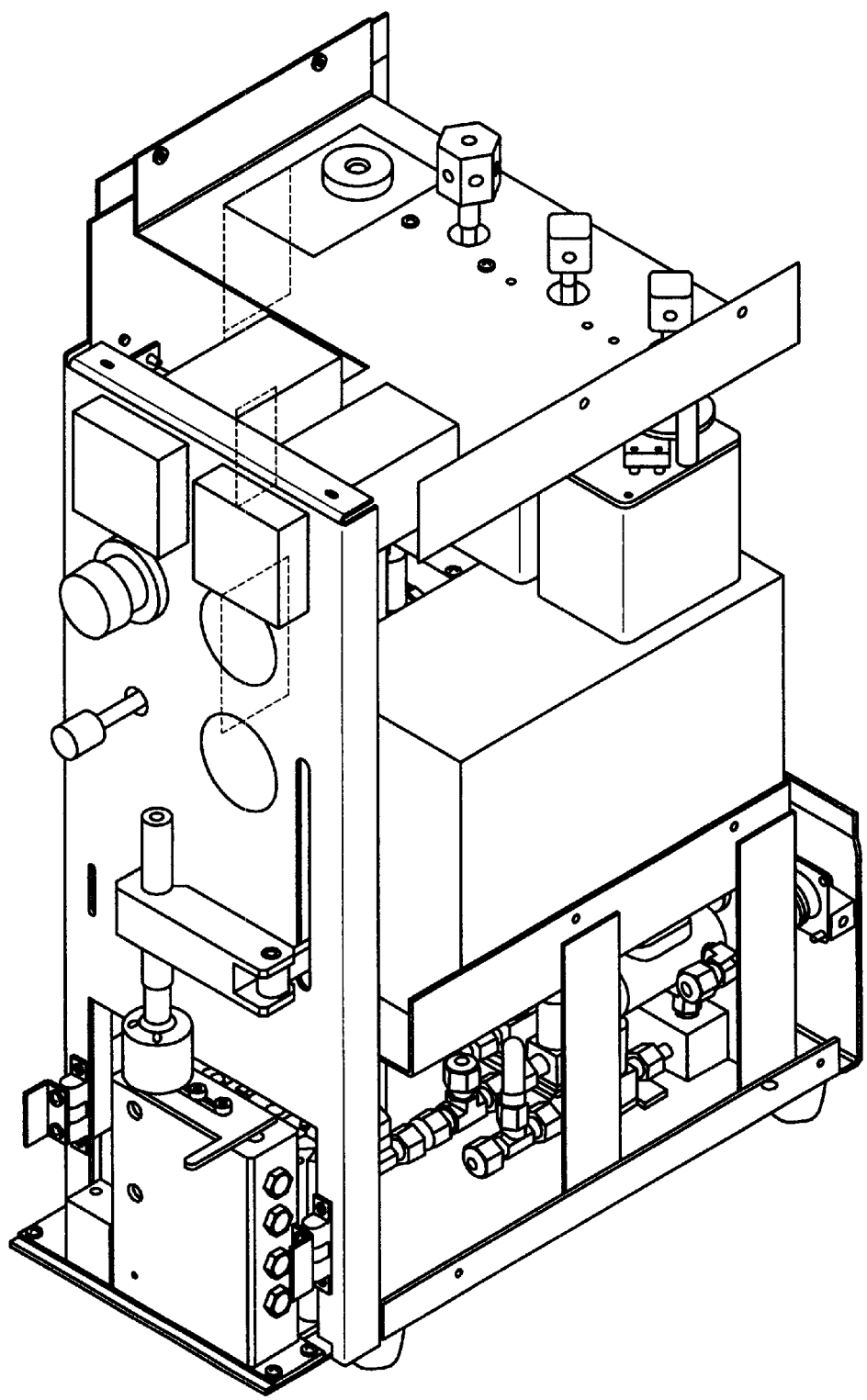
FIG. 1 is a perspective view of a module in which the apparatus for processing radionuclides of the present invention is employed.
Figure 4:
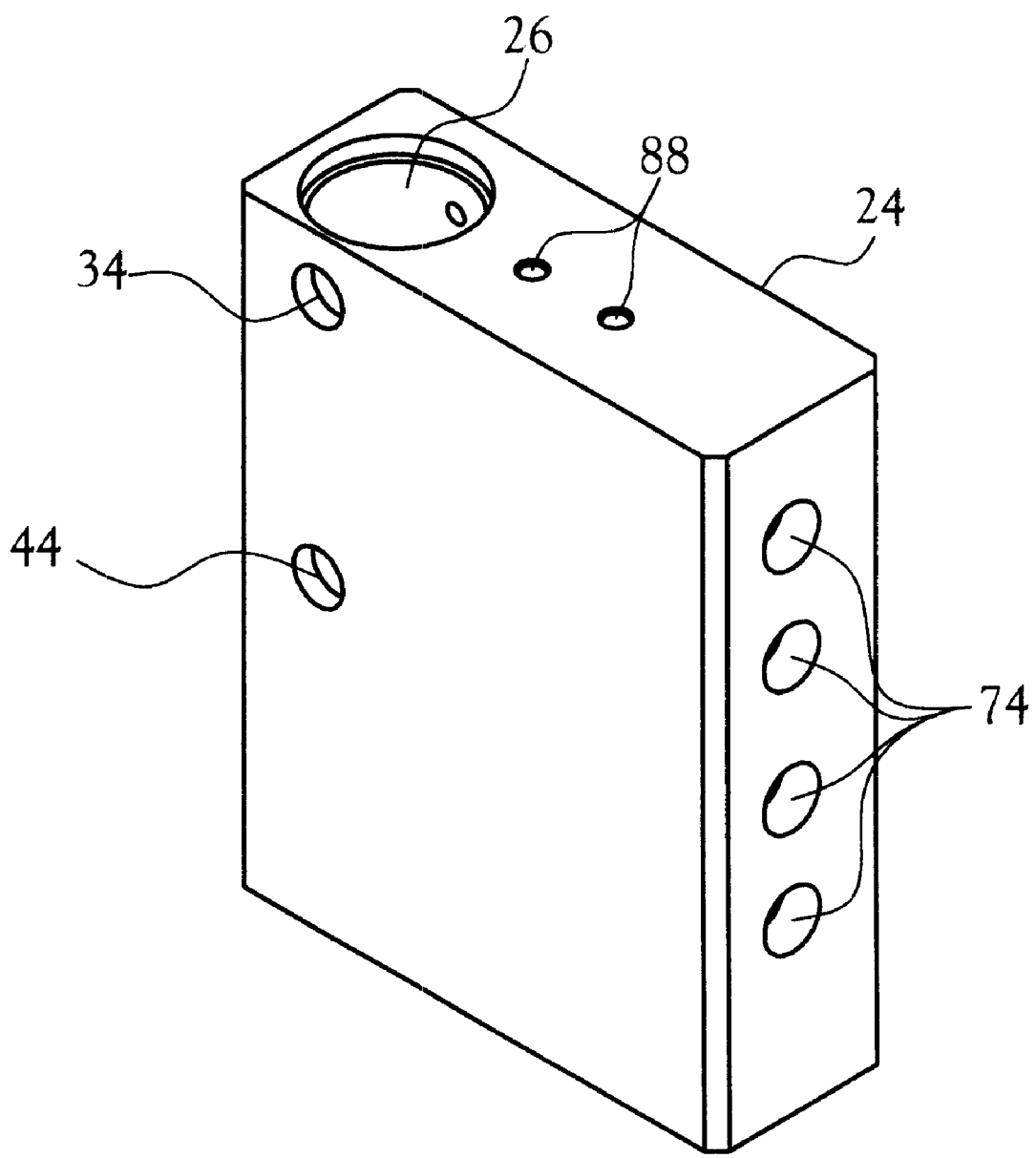
FIG. 4 illustrates a perspective view of heating/cooling block.

As shown in FIG. 1, the apparatus for processing radionuclides of the present invention is typically employed in a processing module 200 to fully automate the synthesis process. The apparatus 10 generally includes a heater/cooler block 24 or block which is configured to receive a reaction vessel 12 therein. In the preferred embodiment, the block 24 is fabricated from a thermally, low conductive material such as teflon or a teflon composite.

Referring to FIG. 2, the reaction vessel 12 is comprised of a test tube 14 and a cover 18 secured to the top 16 of the test tube 14. Preferably, the test tube 14 defines a threaded portion at its opening and the cover 18 is threaded to screw onto the threaded portion of the test tube 14. Further, in the preferred embodiment, the test tube 14 is a commercially available test tube fabricated from borosilicate. The cover 18 defines at least a central port 20 and most preferably two side ports 22, as well. As shown in FIG. 3, a central port 20 is configured to permit a tube to move therethrough to add fluid to and remove fluid from the test tube 14. One of the side ports 22 provides venting and the other side port 22 is for adding reagents and gas.

Figure 5:
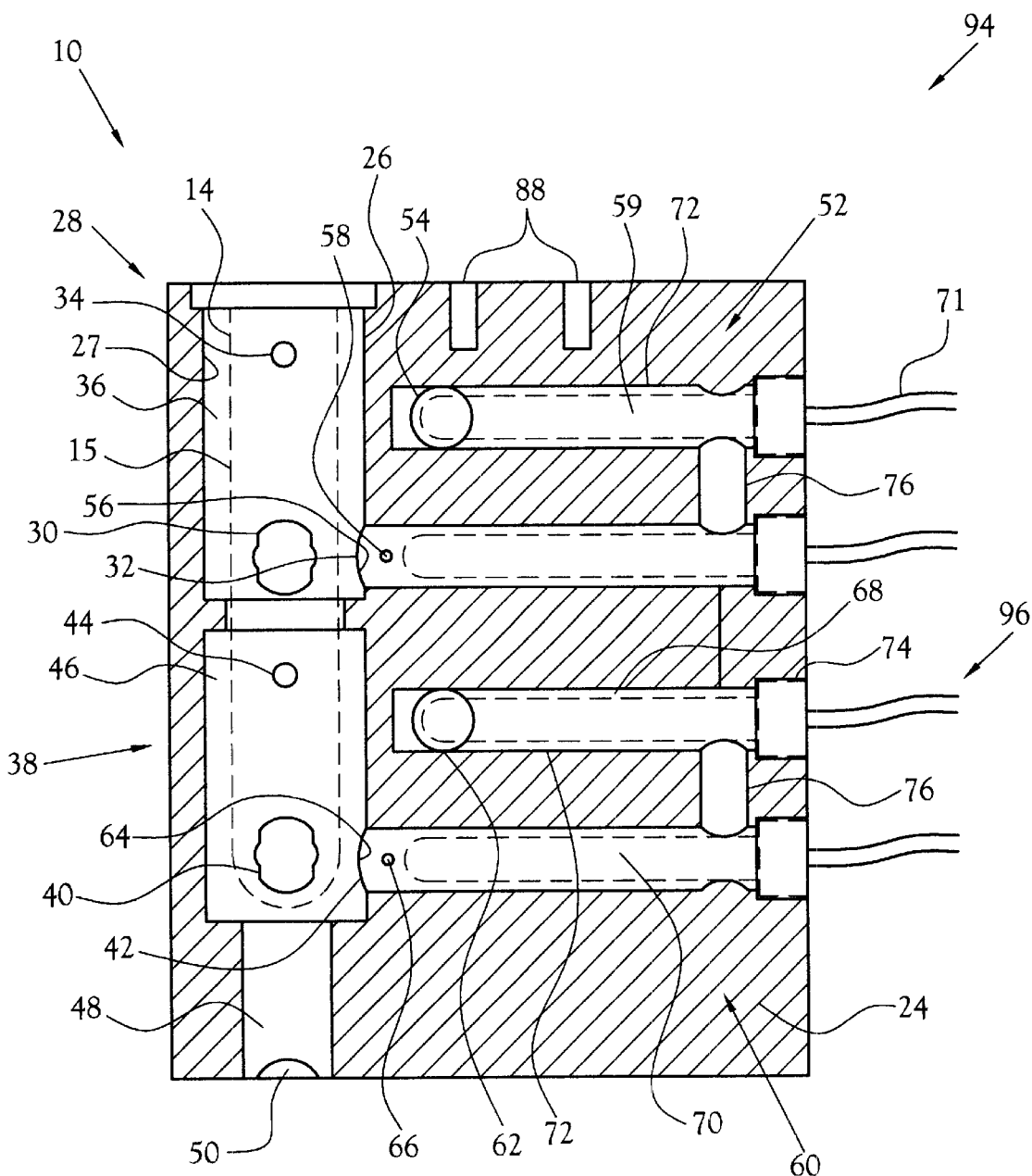
FIG. 5 is a side elevation view, in section, of the heating/cooling block, taken at 5—5 of FIG. 4.

Generally, the block 24 defines a vessel receptacle 26, an upper temperature changing means 94 and a lower temperature changing means 96. The vessel receptacle 26 defines an upper zone 28, a lower zone 38 and a sensing compartment 48. As shown in FIG. 5, the vessel receptacle 26 is configured to receive the test tube 14 of the reaction vessel 12 therein such that there is an upper zone space 36 defined between the exterior 15 of the test tube 14 and the inner wall 27 of the vessel receptacle 26 at the upper zone 28. A lower zone space is defined between the exterior 15 of the test tube 14 and the inner wall 27 of the vessel receptacle 26 at the lower zone 38. The test tube 14 is illustrated, in phantom, in FIG. 5, to indicate the space 36 between the test tube 14 and the inner wall 27 of the vessel receptacle 26. The upper temperature changing means 94 alters the temperature of air in the space 36 in the upper zone 28. The lower temperature changing means 96 alters the temperature of the air in the space 46 in the lower zone 38.

The upper and lower temperature changing means 94, 96 are capable of cooling and heating the air in the spaces 36, 46 of the upper and lower zones 28, 38, respectively, in an independent manner. Referring to FIG. 5, the upper temperature changing means 94 includes an upper heating duct 52 defined by the block 24 and an upper cooling air inlet 30, an upper heating air inlet 32 and an upper gas outlet 34 defined by the vessel receptacle 26. The lower temperature changing means 96 includes a lower heating duct 60 defined by the block 24 and a lower cooling air inlet 40, a lower heating air inlet 42 and a lower gas outlet 44 defined by the vessel receptacle 26. In the preferred embodiment, the cooling air inlets 30, 40 and the heating air inlets 32, 42 are positioned below the respective gas outlets 34, 44, as shown in FIG. 5.

Each of the upper and lower heating ducts 52, 60 defined by the block 24 includes an inlet 54, 62, an outlet 56, 64, and a thermocouple port 58, 66, respectively. Each duct 52, 60 is configured to circulate heated air in the direction from the inlet to the outlet. The upper heating air inlet 32 connects the upper heating duct outlet 56 and the upper zone space 36 to permit air flowing through the upper heating duct 52 to flow into the upper zone space 36, and the lower heating air inlet 42 connects the lower heating duct outlet 64 and lower zone space 46 to permit air flowing through the lower heating duct 60 to flow into the lower zone space 46.

In the preferred embodiment, each duct 52, 60 carries a resistive heater rod 59, 70 therein. The heater rods 59, 70 are supported in their respective upper and lower ducts 52, 60 in a suspended manner such that an air space 68 around the heater rods 59, 70 is defined. The preferred embodiment of the configuration of the heating ducts is illustrated in FIG. 5 wherein each of the upper and lower heating ducts 52, 60 defines two channels 72 which are connected via a conduit 76. The channels 72 are parallel to each other and the conduit 76 is perpendicular to the channels 72. A heater rod 59, 70 is supported in each of the channels 72. More specifically, the block 24 defines four ports 74, each of which communicates with one of the four channels 72. The heater rods 59, 70 can be inserted into each channel 72 via a respective port 74, as illustrated in FIG. 5, in phantom. The port 74 also serves to support the end of the heater rod 59, 70 such that it is suspended in the channel 72. The leads 71 for each heater rod extend from the port 74. It will be noted that although a preferred embodiment for the configuration of the heating ducts 52, 60 is illustrated it is not limited to this configuration.

Moreover, in the preferred embodiment, the block 24 includes a securing device 78 for securely holding the reaction vessel 12 in place in the vessel receptacle 26. The preferred embodiment of the securing device 78 is shown most clearly in FIG. 1 and includes a plate 80 which is slidably mounted to the top of the block 24. More specifically, the plate 80 defines a retaining end 82 and a slot 84. The retaining end 82 is arcuate in configuration to wrap around a portion of the top 16 of the test tube 14. Two bolts 86 pass through the slot 84 of the plate 80 and are positioned in the block 24 in openings 88 shown most clearly in FIG. 5. The top of the bolts 86 are spaced apart from the top of the block 24 and the slot 84 defines a length such that the plate 80 can slide back and forth. Further, it is preferable that the plate 80 define a handle 90 for gripping. The handle 90 is positioned at the end of the plate opposite the retaining end 82.

The apparatus for processing radionuclides 10 is used to effect chemical conversions and processing by heating and/or cooling small amounts of reagents and solvents contained in the reaction vessel 12. The upper and lower zones 28, 38 serve as two separate temperature zones. The upper and lower temperature changing means 94, 96 provide the capability of separately cooling and/or heating the upper and lower portions of the reaction vessel 12 thereby allowing one to perform chemical processes, such as evaporation, nucleophilic substitution, hydrolysis and reflux, over a temperature range from approximately 0° C.–200° C. Heating is effected with the use of forced air to utilize convective heat transfer. More specifically, any or all of the heater rods 59, 70 are activated and air is circulated past the hot rods. Air is injected through the upper and lower heating duct inlets 54, 62 and circulates through the channels 72, past the heater rods 59, 70, where the air heats up via the activated heater rods, 59, 70 and exits through the upper and lower heating duct outlets 56, 64, respectively, and into the upper and lower heating air inlets 32, 42 of the vessel receptacle 26, respectively. The hot air circulates in the upper zone and lower zone spaces 36,46 between the test tube 14 and the block 24 and heats up the test tube 14 to heat the contents of the test tube 14. The hot air in the upper zone space 36 exits via the upper gas outlet 34 and the hot air in the lower zone space 46 exits via the lower gas outlet 44. It will be noted that the heating rods 59 for the upper zone 28 and the heating rods 70 for the lower zone 38 and air flow through the respective zones 28, 38 are independently controlled Cool air is injectable into the upper and lower zone spaces 36, 46 via a cool air source. In the preferred embodiment, cooling is effected by a vortex cooler 112 wherein an inlet stream of compressed air is converted into two streams of air, one cold and one hot. The cold air stream is injected into the space 36, 46 between test tube 14 and block 24 in the upper and lower zones 28, 38 via the upper and lower cooling air inlets 30, 40, respectively. The cold air circulates through the respective spaces 36, 46 and exits via the upper and lower gas outlets 34, 44, respectively. It will be noted that the cool air flow through the respective zones 28, 38 is independently controllable.

Figure 6:
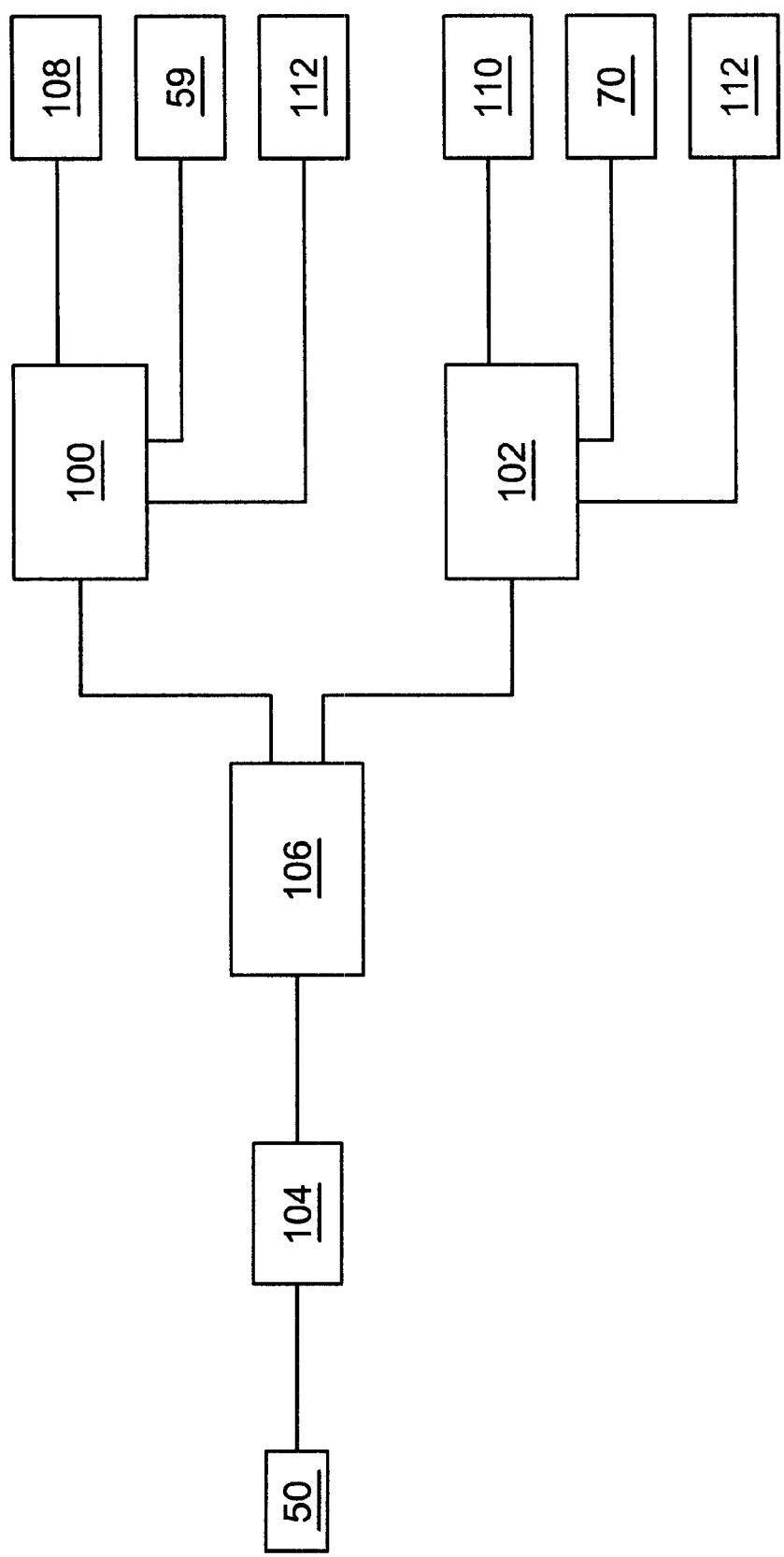
FIG. 6 is a simplified controller schematic for the heater cooler block.

Upper and lower thermocouples 108, 110 are positioned proximate the upper and lower heating air inlets 32, 42 at the upper and lower thermocouple ports 58, 66 to monitor the temperature of the air in the space 36, 46 in the upper and lower zones 28, 38, respectively. The upper and lower thermocouples 108, 110 relay their temperature information to separate temperature controllers 100, 102, as shown in the block schematic of FIG. 6. The upper temperature controller 100 utilizes this information to control the hot air input via the heater rods 59 and the cool air input via the vortex cooler 112 to the upper zone space 36. The lower temperature controller 102 serves the same purpose for the lower zone space 46.

The sensor compartment 48 is situated below the lower zone 38 and houses an infrared sensor 50 therein which is directed upward. More specifically, the infrared sensor 50 is directed at the bottom of the test tube 14 situated in the vessel receptacle to provide real-time temperature measurements of the reaction mixture in the test tube. This technique is non-contact (i.e., does not contaminate the reaction mixture), and allows direct feedback of temperature shifts resulting from changes in process conditions. Information from the infrared sensor 50 is fed to a third temperature controller 104. This information is relayed to a computer 106 which monitors the temperature detected by the infrared sensor 50 and subsequently controls the upper and lower temperature controllers 100, 102, when necessary, to provide cool air or hot air to either or both of the zones 28, 38.

By way of example, one method of producing FDG utilizing the apparatus 10 of the present invention is discussed below. The reaction vessel 12 is positioned in the vessel receptacle 26 and secured in position via the securing device 78. Raw material from the cyclotron is delivered into the reaction vessel 26 via a tube inserted through the central port 20 of the cover 18 of the reaction vessel 12. The raw material is evaporated to make it suitable for reaction. A reagent is added via a side port 22 to react with the evaporated raw material to produce a radioactive intermediate. The liquid is removed from the radioactive intermediate. The radioactive intermediate is hydrolysized and finally purified.

The preparation of the raw material by evaporation is a particularly important step which can greatly effect the final yield. Specifically, it is desirable to know exactly when the raw material is completely evaporated such that the reaction vessel 12 can be cooled to prevent extended heating and overheating of the raw material. In the prior art, one relied on a specific amount of time elapsing and the assumption that, after this time, the raw material had evaporated. With the apparatus 10 of the present invention, the infrared sensor 50 detects the temperature of the test tube 14. The glass of test tube 14 will remain at the temperature of the boiling point of the raw material until the raw material is completely evaporated. Once the raw material is evaporated, the glass of the test tube 14 will heat up to the air temperature in the space 46 surrounding the bottom of the test tube. By employing the infrared sensor 50, one can determine within a matter of seconds when complete evaporation has taken place, at which time the air can be cooled almost instantly to prevent further heating of the evaporated raw material, thereby preventing degradation to the raw material due to overheating. The remaining steps in processing are also controllable to the same degree which results in higher yields.

It will be noted that the apparatus of the present invention, when utilized with the appropriate module 200, as shown in FIG. 1, is self cleaning.

From the foregoing description, it will be recognized by those skilled in the art that an apparatus for processing radionuclides offering advantages over the prior art has been provided. Specifically, the apparatus of the present invention provides the combined ability to quickly heat and cool the reaction vessel. The key issues here are the use of vortex coolers, materials with low heat conductivity and forced air to improve heat transfer to glass. This provides for faster processing times and reduces the amount of product lost to undesirable side reactions. Further, the apparatus provides the ability to separately heat and/or cool two different regions of the reaction vessel. This provides enhanced control over reaction conditions, which results in higher yields of product. Moreover, the use of infrared sensing provides real-time temperature measurements of the reaction mixture. This technique is non-contact and allows direct feedback of temperature shifts resulting from changes in process conditions.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention,

We claim:

1. An apparatus for processing radionuclides which utilizes a reaction vessel for processing the radionuclides therein, said apparatus for processing radionuclides comprising:

a block having formed therein a vessel receptacle, an upper temperature changing means and a lower temperature changing means, said vessel receptacle having an upper zone and a lower zone, said vessel receptacle for receiving the reaction vessel therein in a manner such that an upper zone space is defined between an exterior of the reaction vessel and an inner wall of said vessel receptacle in said upper zone and a lower zone space is defined between an exterior of the reaction vessel and an inner wall of said vessel receptacle in said lower zone, said upper temperature changing means for altering the temperature of gas in said upper zone space, said lower temperature changing means for altering the temperature of gas in said lower zone space, said upper temperature changing means and said lower temperature changing means being independently controllable.

2. The apparatus for processing radionuclides of claim 1 wherein said upper temperature changing means includes an upper heating duct formed in said block, said lower temperature changing means including a lower heating duct formed in said block, each of said upper heating duct and said lower heating duct having an inlet and an outlet for circulating a gas in the direction from said inlet to said outlet, said vessel receptacle having an upper heating air inlet which connects said upper zone space and said upper heating duct outlet such that gas flowing from said upper heating duct outlet flows into said upper zone space, said vessel receptacle further including an upper gas outlet for permitting the exit of gas flowing in said upper zone space, said vessel receptacle having a lower heating air inlet which connects said lower zone space and said lower heating duct outlet such that air flowing from said lower heating duct outlet flows into said lower zone space, said vessel receptacle further including a lower gas outlet for permitting the exit of gas flowing in said lower zone space.

3. The apparatus for processing radionuclides of claim 2 wherein each of said upper and lower heating ducts includes at least one heater rod supported therein in a manner such that an air space is defined around said heater rod, each of said heater rods emitting heat to heat up gas flowing in said air space thereby generating hot gas.

4. The apparatus for processing radionuclides of claim 2 wherein each of said upper heating duct and said lower heating duct is comprised of two channels and a conduit, each of said channels being parallel to each other and carrying a heater rod therein, said conduit connecting said two channels, said block having four ports in communication with each of said channels for receiving a heater rod therethrough such that said heater rod extends into one of said channels, each of said ports being configured to support an end of a heater rod such that said heater rod is supported in a suspended manner such that an air space is defined around said heater rod, each of said heater rods emitting heat to heat up air flowing in said air space.

5. The apparatus for processing radionuclides of claim 2 wherein said upper heating duct includes an upper thermocouple port proximate said upper heating duct outlet for receiving an upper thermocouple therethrough which extends into said upper zone space to detect the temperature of the gas therein and transmit the temperature information to an upper temperature controller which controls said upper temperature changing means, said lower heating duct having a lower thermocouple port proximate said lower heating duct outlet for receiving a lower thermocouple therethrough which extends into said lower zone space to detect the temperature of the gas therein and transmit the temperature information to a lower temperature controller which controls said lower temperature changing means.

6. The apparatus for processing radionuclides of claim 1 wherein said upper temperature changing means includes a upper cooling air inlet which connects a cool air source to said upper zone space for flowing a cool gas therein, said block including an upper gas outlet for permitting the exit of gas flowing in said upper zone space, said lower temperature changing means including a lower cooling air inlet defined by said vessel receptacle which connects a cool air source to said lower zone space for flowing a cool gas therein, said block including a lower gas outlet for permitting the exit of gas flowing in said lower zone space.

7. The apparatus for processing radionuclides of claim 1 wherein said vessel receptacle further includes a sensor compartment positioned below said lower zone, an infrared sensor being housed in said sensor compartment and directed upward to detect the temperature of the bottom of the reaction vessel.

8. The apparatus for processing radionuclides of claim 7 wherein said upper zone space includes an upper thermocouple contained therein for monitoring the temperature of the gas in said upper zone space and relaying the temperature information to an upper temperature controller which controls said upper temperature changing means, said lower zone space including a lower thermocouple contained therein for monitoring the temperature of the gas in said lower zone space and relaying the temperature information to a lower temperature controller which controls said lower temperature changing means, said infrared sensor transmitting temperature information to a third temperature controller which controls said upper and lower temperature controllers thereby controlling said upper temperature changing means and said lower temperature changing means.

9. An apparatus for processing radionuclides which utilizes a reaction vessel for processing the radionuclides therein, said apparatus for processing radionuclides comprising:
    a block having formed therein
        a vessel receptacle having an upper zone and a lower zone, said vessel receptacle for receiving the reaction vessel therein in a manner such that an upper zone space is defined between an exterior of the reaction vessel and an inner wall of said vessel receptacle in said upper zone and a lower zone space is defined between an exterior of the reaction vessel and inner wall of said vessel receptacle in said lower zone,
        an upper temperature changing means for altering the temperature of gas in said upper zone space, said upper temperature changing means including an upper heating duct formed in said block and an upper heating air inlet, an upper cooling air inlet and an upper gas outlet communicating with said vessel receptacle at said upper zone, said upper heating duct having an inlet and an outlet for circulating hot gas in a direction from said upper heating duct inlet to said upper heating duct outlet, said upper heating air inlet connecting said upper zone space and said upper heating duct outlet such that hot gas flowing from said upper heating duct outlet flows into said upper zone space, said upper cooling air inlet connecting an upper cool air source to said upper zone space for flowing a cool gas into said upper zone space, said upper gas outlet for permitting the exit of gas flowing in said upper zone space,
        a lower temperature changing means for altering the temperature of gas in said lower zone space, said lower temperature changing means including a lower heating duct formed in said block and a lower heating air inlet, a lower cooling air inlet and a lower gas outlet communicating with said vessel receptacle at said lower zone, said lower heating duct having an inlet and an outlet for circulating hot gas in the direction from said lower heating duct inlet to said lower heating duct outlet, said lower heating air inlet connecting said lower zone space and said lower heating duct outlet such that hot gas flowing from said lower heating duct outlet flows into said lower zone space, said lower cooling air inlet connecting a lower cool air source to said lower zone space for flowing a cool gas into said lower zone space, said lower gas outlet for permitting the exit of gas flowing in said lower zone space.

10. The apparatus for processing radionuclides of claim 9 wherein each of said upper and lower heating ducts includes at least one heater rod supported therein in a manner such that an air space is defined between said at least one heater rod and an inside wall of said upper and lower heating ducts, each of said at least one heater rods emitting heat to heat up air flowing in said air space thereby generating hot gas.

11. The apparatus for processing radionuclides of claim 9 wherein each of said upper heating duct and said lower heating duct is comprised of two channels and a conduit, each of said channels being parallel to each other and carrying a heater rod therein, said conduit connecting said two channels, said block having four ports in communication with each of said channels for receiving a heater rod therethrough such that said heater rod extends into one of said channels, each of said ports being configured to support an end of a heater rod such that said heater rod is supported in a suspended manner such that an air space is defined around said heater rod, each of said heater rods emitting heat to heat up air flowing in said air space.

12. The apparatus for processing radionuclides of claim 9 wherein said upper heating duct has an upper thermocouple port proximate said upper heating duct outlet for receiving an upper thermocouple therethrough which extends into said upper zone space to detect the temperature of the gas therein and transmits the temperature information to an upper temperature controller to control a flow of hot gas through said upper heating duct outlet and to control a flow of cool gas from said upper cool air source, said lower heating duct having a lower thermocouple port proximate said lower heating duct outlet for receiving a lower thermocouple therethrough which extends into said lower zone space to detect the temperature of the gas therein and transmits the temperature information to a lower temperature controller to control a flow of hot gas from said lower heating duct outlet and to control a flow of cool gas from said lower cool air source.

13. The apparatus for processing radionuclides of claim 12 wherein said vessel receptacle further includes a sensor compartment positioned below said lower zone, an infrared sensor being housed in said sensor compartment and directed upward to detect the temperature of the bottom of the reaction vessel, said infrared sensor transmitting temperature information to a third temperature controller which controls said upper and lower temperature controllers.

14. An apparatus for processing radionuclides comprising:
a reaction vessel including a test tube and a cover secured to a top portion of said test tube, said cover defining at least one opening for receiving an input tube therethrough such that raw materials, reagents, gases and products can be introduced into or removed from said test tube,
a block having formed therein
a vessel receptacle having an upper zone and a lower zone, said vessel receptacle for receiving said test tube therein in a manner such that an upper zone space is defined between an exterior of the test tube and an inner wall of said vessel receptacle in said upper zone and a lower zone space is defined between an exterior of the test tube and inner wall of said vessel receptacle in said lower zone,
an upper temperature changing means for altering the temperature of gas in said upper zone space, said upper temperature changing means including an upper heating duct formed by said block and an upper heating air inlet, an upper cooling air inlet and an upper gas outlet communicating with said vessel receptacle at said upper zone, said upper heating duct having an inlet and an outlet for circulating hot gas in a direction from said upper heating duct inlet to said upper heating duct outlet, said upper heating air inlet connecting said upper zone space and said upper heating duct outlet such that hot gas flowing from said upper heating duct outlet flows into said upper zone space, said upper cooling air inlet connecting an upper cool air source to said upper zone space for flowing a cool gas into said upper zone space, said upper gas outlet for permitting the exit of gas flowing in said upper zone space,
a lower temperature changing means for altering the temperature of gas in said lower zone space, said lower temperature changing means including a lower heating duct formed in said block and a lower heating air inlet, a lower cooling air inlet and a lower gas outlet communicating with said vessel receptacle at said lower zone, said lower heating duct having an inlet and an outlet for circulating hot gas in the direction from said lower heating duct inlet to said lower heating duct outlet, said lower heating air inlet connecting said lower zone space and said lower heating duct outlet such that hot gas flowing from said lower heating duct outlet flows into said lower zone space, said lower cooling air inlet connecting a lower cool air source to said lower zone space for flowing a cool gas into said lower zone space, said lower gas outlet for permitting the exit of gas flowing in said lower zone space.

15. The apparatus for processing radionuclides of claim 14 wherein each of said upper and lower heating ducts includes at least one heater rod supported therein in a manner such that an air space is defined around said heater rod, each of said heater rods emitting heat to heat up air flowing in said air space thereby generating hot gas.

16. The apparatus for processing radionuclides of claim 14 wherein each of said upper heating duct and said lower heating duct is comprised of two channels and a conduit, each of said channels being parallel to each other and carrying a heater rod therein, said conduit connecting said two channels, said block having four ports in communication with each of said channels for receiving a heater rod therethrough such that said heater rod extends into one of said channels, each of said ports being configured to support an end of a heater rod such that said heater rod is supported in a suspended manner such that an air space is defined around said heater rod, each of said heater rods emitting heat to heat up air flowing in said air space.

17. The apparatus for processing radionuclides of claim 14 wherein said upper heating duct including an upper thermocouple port proximate said upper heating duct outlet for receiving an upper thermocouple therethrough which extends into said upper zone space to detect the temperature of the gas therein and transmits the temperature information to an upper temperature controller to control a flow of hot gas through said upper heating duct outlet and to control a flow of cool gas from said upper cool air source, said lower heating duct including a lower thermocouple port proximate said lower heating duct outlet for receiving a lower thermocouple therethrough which extends into said lower zone space to detect the temperature of the gas therein and transmits the temperature information to a lower temperature controller to control a flow of hot gas from said lower heating duct outlet and to control a flow of cool gas from said lower cool air source.

18. The apparatus for processing radionuclides of claim 17 wherein said vessel receptacle further includes a sensor compartment positioned below said lower zone, an infrared sensor being housed in said sensor compartment and directed upward to detect the temperature of the bottom of said test tube, said infrared sensor transmitting temperature information to a third temperature controller which controls said upper and said lower temperature controllers.

19. An apparatus for processing radionuclides which utilizes a reaction vessel for processing the radionuclides therein, said apparatus comprising:
a block having a first surface and a second surface;
a vessel receptacle formed in said block, said vessel receptacle adapted to receive a reaction vessel, said vessel receptacle having an upper zone and a lower zone, said reaction vessel in said vessel receptacle substantially isolating said upper zone from said lower zone;

a first heating duct formed in said block and connecting said first zone to a first heating duct inlet;

a first zone outlet formed in said block and connecting said first zone to said first surface of said block;

a first zone cooling inlet formed in said block and connecting said second surface of said block to said first zone;

a first heater positioned in said first heating duct, whereby a first zone temperature is controlled by forcing a first gas through said first heating duct and by forcing a second gas through said first zone cooling inlet, said first and second gases exhausting through said first zone outlet;

a second heating duct formed in said block and connecting said second zone to a second heating duct inlet;

a second zone outlet formed in said block and connecting said second zone to said first surface of said block;

a second zone cooling inlet formed in said block and connecting said second surface of said block to said second zone; and a second heater positioned in said second heating duct, whereby a second zone temperature is controlled by forcing a third gas through said second heating duct and by forcing a fourth gas through said second zone cooling inlet, said third and fourth gases exhausting through said second zone outlet.

20. The apparatus of claim 19 further including a sensor compartment positioned proximate an inside end of said vessel receptacle, said sensor compartment containing an infrared sensor for monitoring a reaction vessel temperature.

21. The apparatus of claim 19 further including a temperature sensor positioned proximate a junction of said first heating duct and said first zone.

22. The apparatus of claim 19 further including a temperature sensor positioned proximate a junction of said second heating duct and said second zone.

23. The apparatus of claim 19 further including a temperature sensor positioned proximate a junction of said first heating duct and said first zone, and a temperature sensor positioned proximate a junction of said second heating duct and said second zone.

* * * * *